US007328276B2

(12) United States Patent  
Alisuag

(10) Patent No.: US 7,328,276 B2  
(45) Date of Patent: Feb. 5, 2008

(54) COMPUTER ORIENTED RECORD ADMINISTRATION SYSTEM

(75) Inventor: Cora Alisuag, Washington, DC (US)

(73) Assignee: CoraNet Solutions, LLC, Bethesda, MD (US)

( * ) Notice: Subject to any disclaimer, the term of this patent is extended or adjusted under 35 U.S.C. 154(b) by 925 days.

(21) Appl. No.: 10/025,316

(22) Filed: Dec. 18, 2001

(65) Prior Publication Data

US 2002/0083192 A1    Jun. 27, 2002

Related U.S. Application Data

(60) Provisional application No. 60/256,781, filed on Dec. 18, 2000.

(51) Int. Cl.  
*G06F 15/16* (2006.01)

(52) U.S. Cl. .................. 709/237; 713/156; 707/10; 705/76

(58) Field of Classification Search ........... 709/219, 709/230, 227, 206, 225, 237, 203; 726/5; 713/172, 186, 165, 156, 176, 175; 455/411, 455/445; 379/93

See application file for complete search history.

(56) References Cited

U.S. PATENT DOCUMENTS

| | | | | |
|---|---|---|---|---|
| 4,438,824 | A | | 3/1984 | Mueller-Schloer ............ 380/23 |
| 4,868,376 | A | | 9/1989 | Lessin et al. ................. 235/492 |
| 4,926,480 | A | | 5/1990 | Chaum ............................. 380/23 |
| 4,993,068 | A | | 2/1991 | Piosenka et al. .............. 380/23 |
| 5,027,401 | A | | 6/1991 | Soltesz .......................... 380/54 |
| 5,204,670 | A | * | 4/1993 | Stinton ......................... 340/10.5 |
| 5,465,082 | A | | 11/1995 | Chaco ...................... 340/825.54 |
| 5,499,293 | A | * | 3/1996 | Behram et al. ................ 705/76 |
| 5,530,232 | A | | 6/1996 | Taylor .......................... 235/380 |
| 5,535,276 | A | * | 7/1996 | Ganesan ....................... 713/155 |
| 5,578,808 | A | | 11/1996 | Taylor .......................... 235/380 |
| 5,613,012 | A | | 3/1997 | Hoffman et al. ............. 382/115 |
| 5,748,735 | A | * | 5/1998 | Ganesan ....................... 713/165 |
| 5,763,862 | A | | 6/1998 | Jachimowicz et al. ....... 235/380 |
| 5,764,789 | A | | 6/1998 | Pare, Jr. et al. .............. 382/115 |
| 5,801,364 | A | * | 9/1998 | Kara et al. .................... 235/375 |
| 5,805,719 | A | | 9/1998 | Pare, Jr. et al. .............. 382/115 |
| 5,819,240 | A | * | 10/1998 | Kara ............................ 705/408 |

(Continued)

OTHER PUBLICATIONS

CORBAmed Security White Paper—Wilson, Beznosov (1997) ftp.omg.org/pub/docs/corbamed/97-11-03.pdf.*  
The SIMON Architecture: Distributing Data, Tasks..—Norris.. (1999) www.ifs.tuwien.ac.at/~silvia/caic/caic99-03.pdf.*  
Integrating Health Care Information Using XML-Based Metadata—Bird, Goodchild, Beale (2000) staff.dstc.edu.au/andrewg/papers/HIC2000/HIC2000.pdf.*

(Continued)

*Primary Examiner*—Thong Vu  
(74) *Attorney, Agent, or Firm*—Raggio & Dinnin, P.C.

(57) ABSTRACT

A portable memory element containing encrypted data is operatively connected to a first client, and the person associated with the portable memory element provides passcode information necessary to access the encrypted data, wherein the passcode information can be either alphanumeric or biometric, e.g. a fingerprint. The first client communicates with a server, which returns a passkey if the passcode information is authentic for the portable memory element. The first user of the first client then communicates, via a separate communications path, the passkey to a second user of a second client also in communication with the server, who then provides the passkey to the server. If the passkey provided by the second user is valid, the server provides for communication between the first and second clients, and enables the second client to access the portable memory element.

43 Claims, 5 Drawing Sheets

U.S. PATENT DOCUMENTS

| | | | | |
|---|---|---|---|---|
| 5,822,544 | A | 10/1998 | Chaco et al. | 395/202 |
| 5,832,488 | A | 11/1998 | Eberhardt | 707/10 |
| 5,838,812 | A | 11/1998 | Pare, Jr. et al. | 382/115 |
| 5,864,667 | A * | 1/1999 | Barkan | 726/10 |
| 5,867,795 | A | 2/1999 | Novis et al. | 455/566 |
| 5,870,723 | A | 2/1999 | Pare, Jr. et al. | 705/39 |
| 5,933,498 | A | 8/1999 | Schneck et al. | 380/4 |
| 5,943,423 | A | 8/1999 | Muftic | 380/25 |
| 5,944,794 | A * | 8/1999 | Okamoto et al. | 709/225 |
| 5,974,417 | A | 10/1999 | Bracho et al. | 707/10 |
| 5,995,965 | A * | 11/1999 | Experton | 707/10 |
| 6,006,238 | A | 12/1999 | Packard | 707/200 |
| 6,006,274 | A | 12/1999 | Hawkins et al. | 709/249 |
| 6,011,858 | A | 1/2000 | Stock et al. | 382/115 |
| 6,012,636 | A | 1/2000 | Smith | 235/380 |
| 6,041,412 | A | 3/2000 | Timson et al. | 713/200 |
| 6,042,005 | A | 3/2000 | Basile et al. | 235/382 |
| 6,044,349 | A | 3/2000 | Tolopka et al. | 705/1 |
| 6,140,936 | A | 10/2000 | Armstrong | 340/825.34 |
| 6,154,879 | A | 11/2000 | Pare, Jr. et al. | 902/3 |
| 6,189,096 | B1 * | 2/2001 | Haverty | 713/155 |
| 6,345,288 | B1 * | 2/2002 | Reed et al. | 709/201 |
| 6,466,781 | B1 * | 10/2002 | Bromba et al. | 455/411 |
| 6,484,260 | B1 * | 11/2002 | Scott et al. | 713/186 |
| 6,510,513 | B1 * | 1/2003 | Danieli | 713/156 |
| 6,510,523 | B1 * | 1/2003 | Perlman et al. | 726/6 |
| 6,597,770 | B2 * | 7/2003 | Walker et al. | 379/93.12 |
| 6,602,469 | B1 * | 8/2003 | Maus et al. | 422/68.1 |
| 6,615,253 | B1 * | 9/2003 | Bowman-Amuah | 709/219 |
| 6,615,264 | B1 * | 9/2003 | Stoltz et al. | 709/227 |
| 6,658,254 | B1 * | 12/2003 | Purdy et al. | 455/445 |
| 6,789,193 | B1 * | 9/2004 | Heiden | 713/175 |
| 6,792,547 | B1 * | 9/2004 | Murata et al. | 726/5 |
| 6,801,946 | B1 * | 10/2004 | Child et al. | 709/230 |
| 6,816,970 | B2 * | 11/2004 | Morgan et al. | 713/183 |
| 6,866,586 | B2 * | 3/2005 | Oberberger et al. | 463/42 |
| 6,912,578 | B1 * | 6/2005 | Hanko et al. | 709/227 |
| 6,928,547 | B2 * | 8/2005 | Brown et al. | 713/186 |
| 6,928,558 | B1 * | 8/2005 | Allahwerdi et al. | 713/172 |
| 6,959,085 | B1 * | 10/2005 | Hoffstein et al. | 380/30 |
| 6,976,164 | B1 * | 12/2005 | King et al. | 713/156 |
| 6,988,075 | B1 * | 1/2006 | Hacker | 705/3 |
| 6,990,588 | B1 * | 1/2006 | Yasukura | 713/186 |
| 7,047,411 | B1 * | 5/2006 | DeMello et al. | 713/176 |
| 2002/0010679 | A1 * | 1/2002 | Felsher | 705/51 |
| 2003/0041110 | A1 * | 2/2003 | Wenocur et al. | 709/206 |
| 2003/0097331 | A1 * | 5/2003 | Cohen | 705/39 |
| 2003/0158960 | A1 * | 8/2003 | Engberg | 709/237 |
| 2004/0205344 | A1 * | 10/2004 | Otway et al. | 713/169 |
| 2004/0260657 | A1 * | 12/2004 | Cockerham | 705/76 |
| 2005/0131816 | A1 * | 6/2005 | Britto et al. | 705/39 |
| 2005/0187883 | A1 * | 8/2005 | Bishop et al. | 705/67 |
| 2006/0020783 | A1 * | 1/2006 | Fisher | 713/156 |
| 2006/0034238 | A1 * | 2/2006 | Inoue et al. | 370/338 |
| 2006/0129819 | A1 * | 6/2006 | Hirota et al. | 713/172 |

OTHER PUBLICATIONS

"lyngby"—a modeler's Matlab toolbox for..—Hansen, Nielsen.. (1999) □□eivind.imm.dtu.dk/dist/1999/hansen.hbm99.ps.gz.*

Server Interface; www.cs.indiana.edu/~lunnikri/shared-editor/node14.html.*

Nokia Mobile Phone Bluetooth Setting Guideline ;□□www.ambiocom.com/support/installation/instbt2000/Nokia Pairing.pdf.*

Codelock2; Raven Chao; 1999; users.vnet.net/raven3/muf/raven/codelock2.muf.*

Inherent Vulnerabilities of One-Time Passcode Mechanisms; Cindy Cullen; IEEE 1995.*

Bob Gogligoski and Ed Cuellar, "The SanDisk Personal Tag (P-Tag™): Background Applications Report", 4 pages, Oct. 1999.

SanDisk presentation slides, unknown publication date and author, 5 pages.

Toshiba America Electronic Components, Inc. presentation slides, unknown publication date and author, 18 pages.

David W. Forslund et al, "The Importance of Distributed, Component-Based Healthcare Information Systems: The Role of a Service-Based Architecture", unknown publication date, 4 pages.

Object Management Group, Resource Access Decision Facility Specification, Version 1.0, Apr. 2001, downloaded from Internet via http://www.omg.org on Dec. 13, 2001, 78 pages.

Object Management Group, Clinical Observations Access Service Specification, Version 1.0, Apr. 2001, downloaded from Internet via http://www.omg.org on Dec. 13, 2001, 260 pages.

Object Management Group, Lexicon Query Service Specification, Version 1.0, Jun. 2000, downloaded from Internet via http://www.omg.org on Dec. 13, 2001, 182 pages.

Object Management Group, Person Idenfication Service, Version 1.1, Apr. 2001, downloaded from Internet via http://www.omg.org on Dec. 13, 2001, 138 pages.

"Open e-Med Technologies", downloaded from Internet via "http://www.acl.lanl.gov/telemed/" on Dec. 5, 2000, 1 page.

David Forslund, "TeleMed Introduction", Aug. 19, 2000, downloaded from Internet via "http://www.acl.lanl.gov/telemed/" on Dec. 5, 2 pages.

"Architecture : OpenEMed Virutal Patient System", downloaded from Internet via "http://www.acl.lanl.gov/telemed/" on Dec. 5, 2000, 3 pages.

DavidForslund, "OpenEMed Distributed Objects", downloaded from Internet via "http://www.acl.lanl.gov/telemed/" on Dec. 5, 2000., 2 pages.

David Forslund and Tery Weymouth, "Brief Overview of the PidServer", downloaded from Internet via "http://www.acl.lanl.gov/telemed/" on Dec. 5, 2000, 11 pages.

David Forslund, "Brief Overview of the MedServer", downloaded from Internet via "http://www.acl.lanl.gov/telemed/" on Dec. 5, 2000, 10 pages.

James George, "Authentication and Policy Management in Telemed", downloaded from Internet via "http://www.acl.lanl.gov/telemed/" on Dec. 5, 2000, 13 pages.

"MedTraits",downloaded from Internet via "http://www.acl.lanl.gov/telemed/" on Dec. 5, 2000, 50 pages.

"Technical facts of Precise 100",downloaded from Internet via "http://www.precisebiometrics.com/products/technical_info.html/" on Dec. 5, 2000, 2 pages.

Chinese Patent Office, English translation of First Office Action, dated Feb. 18, 2005, in Chinese Patent Application No. 01 8 20786.3 Based on International Application No. PCT/US01/48996 of Cora Alisuag, Title: Computer Oriented Record Administration System, International Filing Date: Dec. 18, 2001 (English Translation of Cite No. 2).

Chinese Patent Office, First Office Action, dated Feb. 18, 2005, in Chinese Patent Application No. 01 8 20786.3 Based on International Application No. PCT/US01/48996 of Cora Alisuag, Title: Computer Oriented Record Administration System, International Filing Date: Dec. 18, 2001 (Chinese Language).

Chinese Patent Office, English translation of Second Office Action, dated Nov. 4, 2005, in Chinese Patent Application No. 01 8 20786.3 Based on International Application No. PCT/US01/48996 of Cora Alisuag, Title: Computer Oriented Record Administration System, International Filing Date: Dec. 18, 2001 (English Translation of Cite No. 4).

Chinese Patent Office, Second Office Action, dated Nov. 4, 2005, in Chinese Patent Application No. 01 8 20786.3 Based on International Application No. PCT/US01/48996 of Cora Alisuag, Title: Computer Oriented Record Administration System, International Filing Date: Dec. 18, 2001 (Chinese Language).

Canadian Patent Office, Office Action dated Jul. 17, 2006 in Canadian Patent Application No. 2,432,141, Title: Computer Oriented Record Administration System, International Filing Date: Dec. 18, 2001.

* cited by examiner

Fig. 5

| Data Type | I<br>VISTA SYSTEM | II<br>CHCS | III-A<br>Private Sector<br>Inpatient/Outpatient Services | III-B<br>Private Sector<br>Emergency Services |
|---|---|---|---|---|
| Appointment System |  | X | X |  |
| Patient Record System | X |  | X |  |
| Dentistry | X |  |  |  |
| Dietetics | X |  |  |  |
| Hospital Based Home Care | X |  |  |  |
| Immunology Case Registry | X |  |  |  |
| Integrated Imaging System | X |  |  |  |
| Laboratory | X | X | X | X |
| Medicine | X |  | X |  |
| Mental health | X |  |  |  |
| Network Health Exchange | X |  |  |  |
| Nursing | X |  |  |  |
| Oncology | X |  |  |  |
| Pharmacy | X | X | X |  |
| Prosthetics | X |  |  |  |
| QUASAR | X |  |  |  |
| Radiology/Nuclear Medicine | X | X | X |  |
| Remote Order Entry | X |  |  |  |
| Social Work | X |  |  |  |
| Spinal Cord Dysfunction Registry | X |  |  |  |
| Surgery | X |  | X |  |
| Patient Administration |  | X |  |  |
| Medical Services Accounting |  | X |  |  |
| Clinical |  | X |  |  |
| Dietetics |  | X |  |  |
| Facility Quality Assurance |  | X |  |  |
| Managed Care Program |  | X |  |  |
| Insurance Information/Billing |  |  | X | X |
| Personal Information |  |  |  | X |
| Family History |  |  |  | X |
| Past History |  |  |  | X |
| Physical Examination |  |  |  | X |
| Progress Notes |  |  | X | X |
| Emergency Contact |  |  |  | X |

COMPUTER ORIENTED RECORD ADMINISTRATION SYSTEM

CROSS-REFERENCE TO RELATED APPLICATIONS

The instant application claims the benefit of U.S. Provisional Application Ser. No. 60/256,781 filed on Dec. 18, 2000, which is incorporated herein by reference.

BRIEF DESCRIPTION OF THE DRAWINGS

In the accompanying drawings:

FIG. 5 illustrates an example of a data structure on a portable memory element.

DESCRIPTION OF EMBODIMENT(S)

Figure 1:
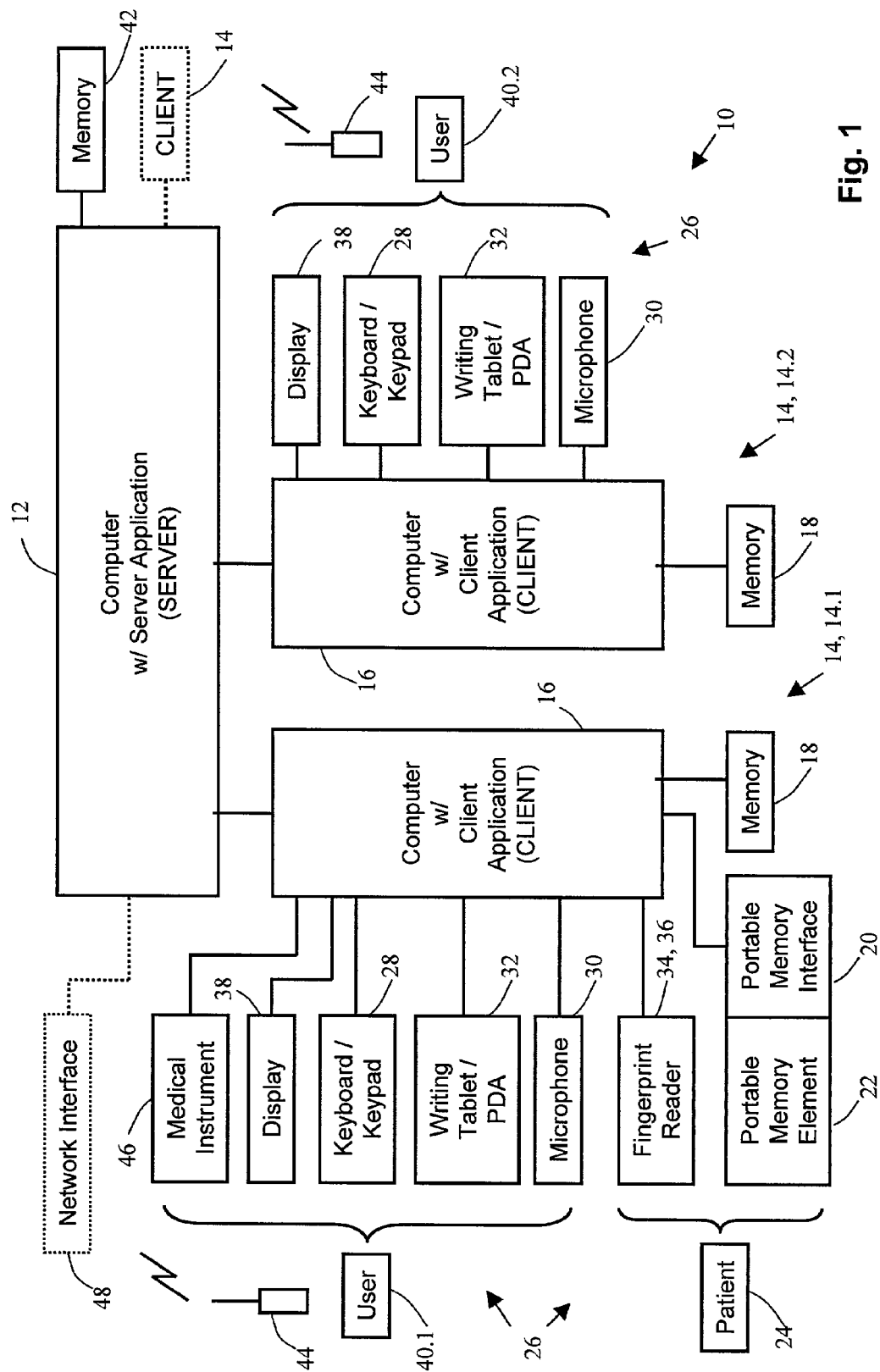
FIG. 1 illustrates an embodiment of a computer oriented record administration system.

Referring to FIG. 1, a computer oriented record administration system 10 comprises a server computer system 12 in communication with at least one client computer system 14, for example, via a network, e.g. the Internet, that may incorporate both wireless and wired or fiber optic interconnections.

A first client computer system 14.1 comprises a computer 16 and a memory 18 operatively connected thereto, wherein the memory 18 contains client application software that runs on the computer and is adapted to interface with a variety of peripherals operatively connected to the computer 16, and to communicate with the server computer system 12. A memory interface device 20 is operatively connected to the computer 16 and is adapted to interface with a portable memory element 22. The portable memory element 22 contains data that is encrypted with a key derived from passcode information that is either known by, or an identifying feature of, the person 24 whose data is recorded on the portable memory element 22. The computer 16 is also operatively connected with at least one data input device 26 through which passcode information may be entered thereto so as to enable the client computer system 14 to read from, or write to, the portable memory element 22. For example, the at least one data input device 26 may comprise a keyboard or keypad 28, a microphone 30 or a writing tablet 32 (e.g. that uses a stylus for input, e.g. a Personal Digital Assistant (PDA), e.g. PALM PILOT or similar device), or a combination thereof. Furthermore, the at least one data input device 26 comprises a biometric input device 34, e.g. a fingerprint reader 36—that can be used to identify the person 24 associated with the portable memory element 22. The computer 16 is also operatively connected with a display 38 for displaying information to a first user 40.1.

A second client computer system 14.2 comprises a computer 16 and a memory 18 operatively connected thereto, wherein the memory 18 contains client application software that runs on the computer and is adapted to interface with a variety of peripherals operatively connected to the computer 16, and to communicate with the server computer system 12. The computer 16 is also operatively connected with at least one data input device 26, for example, comprising a keyboard or keypad 28, a microphone 30 or a writing tablet 32, or a combination thereof. The computer 16 of the second client computer system 14.2 is also operatively connected with a display 38 for displaying information to a second user 40.2.

For example, the computer oriented record administration system 10 illustrated in FIG. 1 may be used for accessing encrypted medical records stored on the portable memory element 22 carried by a patient 24 who is subject to emergency medical care, for example, by 1) a first user 40.1 who is a paramedic, from an ambulance, wherein the first client computer system 14.1 located in the ambulance communicates with the server computer system 12 via wireless communication with a base station that is operatively connected to the Internet, and by 2) a second user 40.2, for example, a doctor in an emergency room of the hospital to which the patient 24 is being transported by the ambulance, who has access to the second client computer system 14.2 located in the emergency room of the hospital or on the person of the emergency room doctor.

Figure 2:
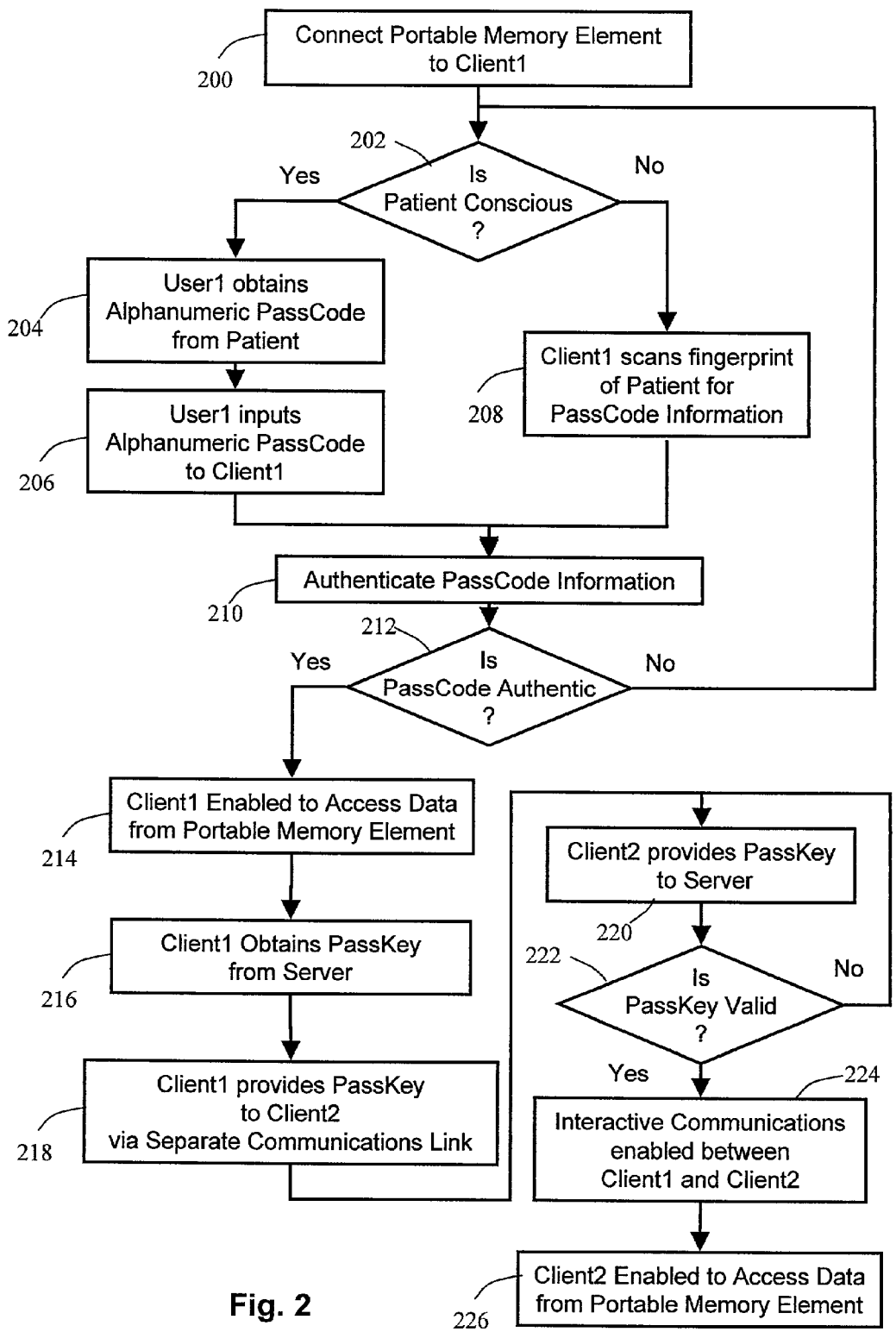
FIG. 2 illustrates a flow chart of the operation of the computer oriented record administration system.

Referring to FIG. 2, a method is illustrated by which the encrypted information on the portable memory element 22 can be accessed by the first user 40.1, and by which the second user 40.2 can also access this information and also communicate with the first user 40.1 and record a dialog therebetween on the portable memory element 22. The portable memory element 22 contains identification and medical information about an associated patient/person 24 who is being treated by the first user 40.1—e.g. a paramedic. The portable memory element 22 is carried by the patient 24, and obtained therefrom by the first user 40.1. In step (200), the first user 40.1 connects the portable memory element 22 to the memory interface device 20. If, in step (202), the patient 24 is conscious, then if convenient and possible, in step (204), the first user 40.1 obtains a passcode from the patient 24 that can be used to read and decrypt information on the portable memory element 22. For example, the passcode could comprise a userid and a password. Then, in step (206), the first user 40.1 enters the passcode information into the first client computer system 14.1, for example via the keyboard or keypad 28, or by voice using the microphone 30. If, from step (202), the patient 24 is either unconscious or unable to provide the passcode information, then, in step (208), one or more fingerprints of the patient 24 are scanned into the first client computer system 14.1, wherein the corresponding passcode information is derived from the one or more fingerprints.

Then, in step (210), the passcode information from either of steps (206) or (208) is authenticated. This authentication process can be performed either by the first client computer system 14.1, or by the server computer system 12 in communication therewith, or by both. In the later case, the passcode information is transmitted in encrypted form from the first client computer system 14.1 to the server computer system 12, and is authenticated with respect to the encrypted passcode information that is stored on the portable memory element 22. Alternately, or additionally, the passcode information may be authenticated with respect to the passcode information stored in a memory 42 of the server computer system 12, corresponding to the patient 24. If, in step (212), the passcode information obtained from the patient 24 is authentic for the portable memory element 22, then in step (214) the first client computer system 14.1 and the corresponding first user 40.1 are enabled to access the data on the portable memory element 22. Otherwise, from step (212), the process repeats with step (202).

Following step (214), if the first user 40.1—e.g. a paramedic—needs to communicate with a second user 40.2—e.g. an emergency room doctor,—e.g. either to share information or to seek advice, then in step (216), the first user 40.1 may obtain a passkey from the server computer system 12, which passkey will serve as a temporary password to enable the second user 40.2 to communicate with the first user 40.1 via the server computer system 12. In step (218), the first user 40.1 provides the passkey to the second user 40.2 via a separate communications channel, e.g. a radio 44 or telephone, e.g. cellular phone. Then, in step (220), the second user 40.2 provides the passkey to the server computer system 12, e.g. via the keyboard or keypad 28, the writing tablet 32 or the microphone 30 of the second client computer system 14.2. If, in step (222), the passkey provided by the second user 40.2 is valid, then, in step (224), interactive communications are enabled between the first 40.1 and second 40.2 users, e.g. via a secure chat room, wherein the messages communicated therebetween may be recorded on the portable memory element 22 and/or in the memory 42 of the server computer system 12. Furthermore, in step (226), the second client computer system 14.2 and the associated second user 40.2 are given access to the data on the portable memory element 22, for example, to the medical records and insurance information of the patient. In addition to the interactive communications—in either voice or text—other information may be recorded on the portable memory element 22 during the interactive communications session. For example, the first user 40.1 could test the patient 24 with one or more medical instruments 46, the data from which could be either be automatically read and stored by the first client computer system 14.1, or recorded by the first user 40.1 in the voice or data communications stream. If, from step (222), the passkey is not valid, then the process repeats with step (220).

Referring again to FIG. 1, one or more other client computer systems 14 may also be in communication with the server computer system 12, and may also be enabled for interactive communications with both the first 14.1 and second 14.2 client computer systems—or any other client computer systems that are already in interactive communication therewith—in accordance with the method illustrated in FIG. 2, replacing references to the second client computer system 14.2 and the associated second user 40.2 with the particular client computer system 14 and its associated user 40. Furthermore, the server computer system 12 may be interfaced with other computer systems via a network interface 48, for example, so as to have access to one or more databases that are distributed across the associated network.

In one embodiment, the computer oriented record administration system 10 may be used to gather, maintain and administer the medial records of a person 24, wherein the person 24 carries with them a portable memory element 22 containing identification and medical records. These medical records could be exclusively located on the portable memory element 22, or these medical records—or a subset or superset thereof—could also be stored in one or more central databases operatively connected to the computer oriented record administration system 10. The portable memory element 22 can also be used for storing other non-medical information that is pertinent to the user, e.g. ID access information for buildings or rooms; library cards; financial information, e.g. credit card information; driver's license information; or food stamp information.

For example, in an exemplary system known as CORA-NET (Computer Oriented Record Administration Network), the associated portable memory element 22 is known as a CORALink (Computer Oriented Record Administration Link) card, and the associated memory interface device 20 is known as a CORALink reader.

The CORALink card—about the size of a credit card—comprises a non-volatile, non-rotating memory using NAND flash memory that, for example, is capable of holding up to 128 MB of stored information that is relatively impervious to most common physical and electromagnetic stress—e.g. from magnetic fields, electromagnetic fields or thermal stress,—and which can be sustained for approximately 100 years.

The CORALink card has been adapted to interface with a variety of types of computer systems, including any Type II PCMCIA reader or parallel interface reader. The CORALink card is both "hot-swappable" and plug and play compatible. The CORALink card, the CORALink reader, and the associated software drivers are compatible with the following operating systems-MS-DOS, Windows 3.X, Windows 95, Windows 98, Windows NT 3.5 & 4.0, Windows CE, Unix Kernel OS, Apple Power Book and Newton OS so as to accommodate a broad range of potential operating environments. The CORALink card is plugged into the CORALink reader, and is opened by plugging the CORALink reader into a PCMCIA (or equivalent) slot of a computer, whereupon the card acts as an extra drive on the computer. The CORALink reader, for example, works with both the 16 and 32 bit PC card interfaces, wherein data can be transferred at 1.2 megabytes per second with the 16 bit interface, and at 11.4 megabytes per second with the 32 bit interface.

The information in the CORALink card is encrypted and compressed, and is accessible by CORANET software on a client computer system 14 upon the authentication of either a password or a fingerprint passcode by which the information on the CORALink card is encrypted. Access to the CORALink card without the proper software and authentication results in the display of the contents of the card as an encrypted read-only file, which prevents unauthorized access and tampering of medical data files. Information contained on the CORALink card can also be duplicated in a central database for purposes of either control or backup.

In the CORANET system, a fingerprint reader 36 is used to read a fingerprint of a cardholder/patient 24 for purposes of accessing the information on the CORALink card. The fingerprint reader 36 used in the exemplary CORANET system is manufactured by Precise Biometrics, incorporates a silicon sensor, and is designed to interface via a standard interface with a computer. An associated Software Development Kit (SDK) provides a set of C functions and data structures packed in a DLL and designed to work with Windows operating systems so as to provide for control of the fingerprint reader 36.

Data on the CORALink card is accessed either via a fingerprint authorization of the card owner, or using a user provided password, wherein the CORALink card reader and the fingerprint reader are each operatively connected to a common computer. The fingerprint reader 36 is principally beneficial for mobile or emergency room settings in which the patient 24 may be unconscious or unable to remember their alphanumeric passcode, although it may also be beneficial in other settings as well.

A platform independent software system enables password/fingerprint protected access of data on the CORALink card. Moreover, secure sharing of these files over the Internet is enabled, as is access and update of these files by medical personnel even when they are not physically present at the scene of the emergency.

When the holder of a CORALink card needs emergency medical assistance, the card is inserted into a computer equipped with a reader by the medical personnel attending the patient. The software that reads the card is invoked and access is granted to the card, either by using name and password, or by a fingerprint match (should the patient be unconscious). The computer with the CORALink card accesses a server on the Internet that enables access to the card's information and returns an authorization passkey that can be used by other medical personnel (doctors) on the web to access information on this card. It is this passkey that allows emergency room (ER) doctors to access the card's information from the hospital computer. After receiving the passkey (transmitted via cellular phone or radio) from the practitioner attending the patient, the doctor uses the dedicated CORANET software and the passkey to access the appropriate Internet site, enabling access to the contents of the card and establishing registered voice contact with the practitioner attending the patient.

Once the doctor has established a secure, passkey verified connection via the Internet with the medical personnel attending the patient, the doctor can request the attendant person to perform particular tests or procedures. CORANET allows for the display of these results on the doctor's computer and allows the doctor to log his/her observations on the card for future reference. When the patient arrives at the hospital, the medical personnel attending the patient hands the card to the doctor who plugs the card directly into a computer and continues to provide necessary medical attention. Logs of all events are maintained, including both voice (e.g., conversation between doctor and practitioner over the system) and electronic conversations/instructions (e.g. requests to perform tests), beginning from when the medical personnel attending the patient connects to the CORANET web server, and continuing until the doctor closes the service session. These logs provide a source of future reference for purposes of quality assurance and medical insurance claims.

Since hospital personnel and offsite personnel (in an ambulance at an accident scene or patient residence) have different medical information requirements, different versions of the CORANET software are provided for different applications. The version of software used by the remote practitioner is called the "Mobile CORANET" (CORANET-M) software and the version used by the doctor at the hospital is called the "Base CORANET" (CORANET-B) software. The interface and capabilities of each version are customized for the different tasks to which each software is targeted. CORANET-M and CORANET-B versions of the software are, for example, developed as JAVA-based software, enabling download and execution from any JAVA enabled web browser. This provides for downloading the software when a prospective user does not have the CORANET software already installed on their computer, although the pre-installation of dedicated software generally is preferred because of bandwidth constraints and the need for speed-of-action.

The medical equipment on board emergency vehicles is, for example, directly interfaced with the onboard computer, allowing for test results to be directly logged, stored on the computer and then transmitted. For some equipment, for example an EKG machine, this might require additional hardware to provide for a computer interface. Data-specific software is provided to store and transmit data.

Figure 3:
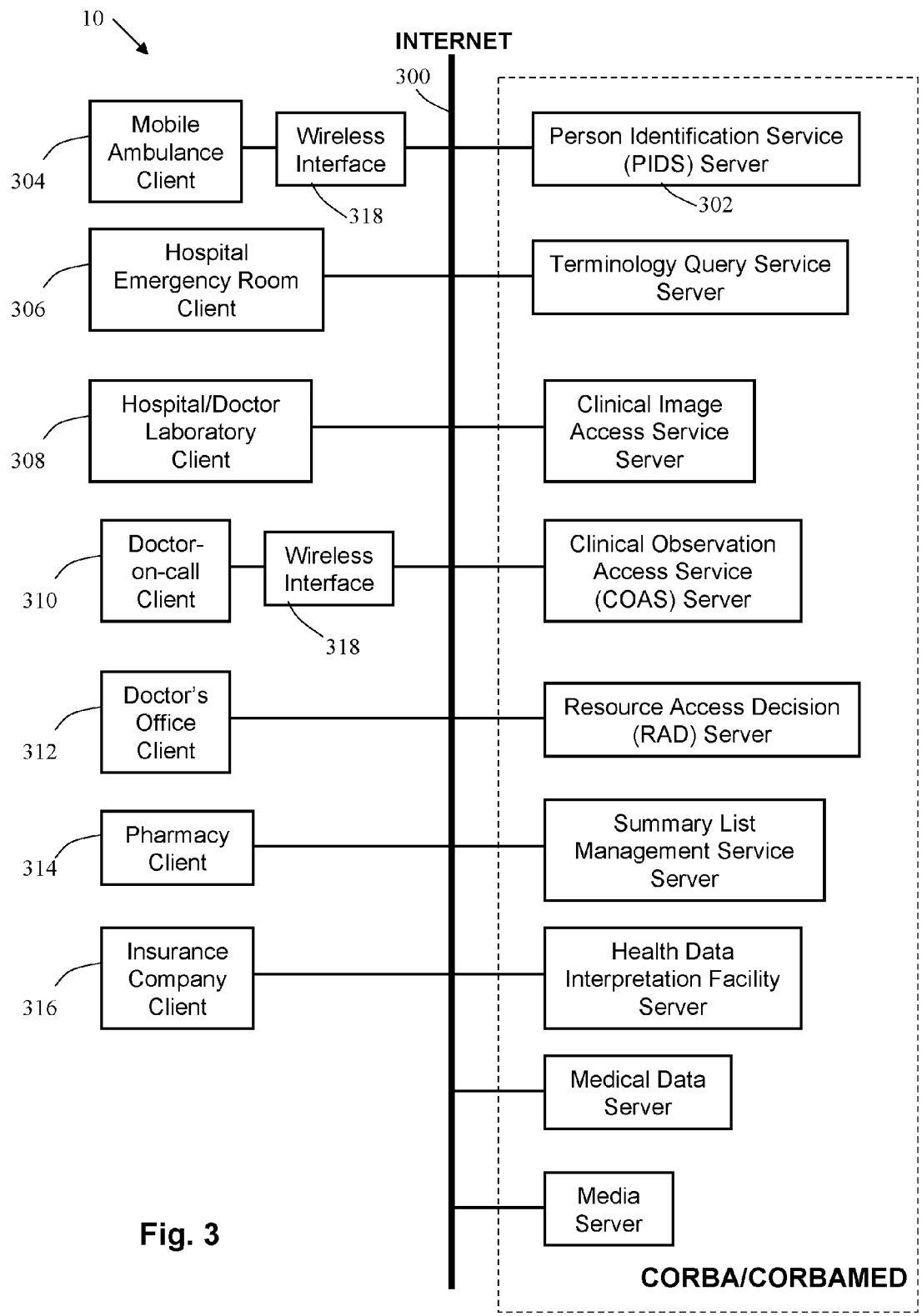
FIG. 3 illustrates another embodiment of a computer oriented record administration system incorporating a Common Object Request Broker Architecture (CORBA) in accordance with a CORBAMED standard.

Referring to FIG. 3, the CORANET software is constructed in accordance with the emergent CORBAMED standards. CORBAMED is the OMG (Object Management Group, Inc.) supported interface for the electronic exchange of medical data (http://www.omg.org/homepages/corbamed/), wherein compliance to the standard facilitates integration of the CORANET system with other medical and administrative software packages. CORBA is an acronym for Common Object Request Broker Architecture, which is a specification for how distributed software applications written in one or more computer languages can operate together over the Internet using language-neutral interface. Several "servers" have been defined within the CORBAMED standard based on the kind of information and services that are shared. These standard severs of CORBAMED include the following:

Personal Identification Service (PIDS): The PIDS server(s) cross-references and identifies users of the medical system. A person typically visits several healthcare professional/provider, most of whom assign and maintain independent patient ID's. In recent years, changes in healthcare industry have made it both increasingly important and at the same time difficult to access the complete medical record of an individual. Risk-shared and capitalization-based reimbursement policies have made it necessary to avoid redundant treatments. Increased specialization of providers has caused increased fragmentation and distribution of patient records. The PIDS specification defines the CORBA interface that organizes person ID management functionality to meet healthcare needs.

The Personal Identification Service (PIDS) is a specification for a CORBA-service that has been developed and made available by the Object Management Group (OMG) on its Web site http://www.omg.org/technology/documents/formal/person_identification_service.htm the documents of which are referenced thereby are incorporated by reference herein. Based on CORBA, the PIDS specification provides a framework for correlating a patient's medical data, which may be stored in a number of different databases located on different computers. Each database that stores medical or other data has its own internal mechanism for locating that data, often based on unique primary keys. A primary key for a given database provides users with the assurance that a single unique record will be returned when a query is made using the key. The difficulty is that each database has its own primary key or other mechanism for locating a patient's data record. The key to a patient's information on one database may have no relationship to the key used to locate the patient's medical information in another database. There may therefore be no way to determine based on a primary key that the data stored in different databases in fact belongs to the same patient.

The PIDS specification addresses the problem of how to access and unify a patient's medical data that is stored in disparate databases. The PIDS service employs a Correlation Manager, by which different databases holding medical information may be linked. In order for the PIDS service to query the various databases to locate a patient's scattered medical records, a set of patient characteristics is submitted to a PIDS server. These patient characteristics are known as traits, and include such items as name, date of birth, sex, nationality, race, and other items. The traits are defined according to the Health Level 7 (HL7) specification. (OMG "Person Identification Service" specification, pp. 2-48 ff. of http://www.omg.org/technology/documents/formal/person- _identification_service.htm) When passed a set of patient traits defined according to this specification, the PIDS server can query multiple databases and can determine based on the traits supplied that the medical records stored in the different databases in fact belong to the same patient. The PIDS server returns a correlated ID, which it uses to tie together the patient's records that have been retrieved by using queries based on the traits.

PIDS is a specification for a service rather than an implementation of one. It defines a set of CORBA interfaces that software applications must implement in order to use the service. The PIDS interfaces may be implemented in a number of computer languages. PIDS servers written in one language can communicate with servers written in a different language, as long as both servers use the CORBA interfaces contained in the specification.

Terminology Query Service: The Terminology Query Service is a specification for a CORBA-service that has been developed and made available by the Object Management Group (OMG) at the Web site http://www.omg.org/technology/documents/formal/lexicon_query_service.htm, the documents of which are referenced thereby are incorporated by reference herein. This service reconciles the different format requests issued by medical systems. The lack of standardization of medical teams becomes even more difficult to reconcile through an electronic exchange of information. This service presents a common interface for a client system to issue equivalence and explanation requests about a term for an information provider system.

Clinical Observation Access Service (COAS): The Clinical Observation Access Service (COAS) is a specification for a CORBA-service that has been developed and made available by the Object Management Group (OMG) at the Web site http://www.omg.org/technology/documents/formal/clinical_observation_access_service.htm the documents of which are referenced thereby are incorporated by reference herein. The objective of COAS is to provide a common interface for healthcare systems exchanging clinical observations. Clinical observations are defined as "any measurement, recording, or description of the anatomical, physiological, pathological, or psychological state or history of a human being or any sample from a human being, and any impressions, conclusions, or judgments made regarding that individual within the context of the current delivery of health care". In layman terms, clinical observations describe a healthcare incident for a patient with its exams, conclusions and outcome.

There are several levels at which a system can conform to the COAS standard. The first level is by implementing the generic interface in one of described subsets. The second level is by being able to understand the data format exchanged by COAS compliant software (currently only one data format is defined), The third and last level is by the definition of observation types supported. Currently the only type definition supported by the standard is the HL7. A generalized information model to describe healthcare definition that is described by the document at the web site: http://www.mcis.duke.edu/standards/HL7/data-model/HL7/modelpage.html, which is incorporated by reference herein.

Clinical Image Access Service (CIAS): The medical community already has an established standard, called the Digital Imaging and Communications in Medicine (DICOM) for image-exchange. The DICOM standard is based on the DICOM information model that helps clarify its semantics. The CIAS is not intended to supplement DICOM; rather, it is intended as a service "wrapper" around portions of DICOM in order to provide access to clinical images and related information where the full richness of DICOM is not required. The CIAS is a clinical image access server intended for applications that do not support diagnosis from the images.

Resource Access Decision (RAD): The Resource Access Decision (RAD) is a specification for a CORBA-service that has been developed and made available by the Object Management Group (OMG) on its Web site http://www.omg.org/technology/documents/formal/resource_access_decision.htm, the documents of which are referenced thereby are incorporated by reference herein. The RAD service is a mechanism for obtaining authorization decisions and administrating access decision policies, providing a common way for applications to request and receive an authorization decision. The current RAD proposed standard is intended to provide the functionality required by healthcare applications that are not already supported on CORBA security standards.

Two additional CORBAMED services, Summary List Management and Health Data Interpretation Facility are also being provided for within CORBAMED.

Whereas FIG. 3 illustrates the various CORBAMED servers as being operatively connected to the Internet 300, it should be understood that different servers can be interfaced using different protocols. The PIDS Server 302 is adapted to function as the server computer system 12 in accordance with the system and method illustrated in FIGS. 1 and 2. The PIDS Server 302 can communicate with a variety of different client computer systems 14 via the Internet 300, including, but not limited to a mobile ambulance client 304; a hospital emergency room client 306; a laboratory client 308 at a hospital, doctor's office or the like; a doctor-on-call client 310, a doctor's office client 312; a pharmacy client 314; or an insurance company client 316. In FIG. 3, the mobile ambulance client 304 and doctor-on-call client 310 are illustrated as being in communication with the internet via an associated wireless interface 318, e.g. a radio, cell phone, or PDA link to a base station that is in communication with the Internet 300. For example, a doctor-on-call could utilize a mutilimedia enabled cell phone or a PDA.

Figure 4:
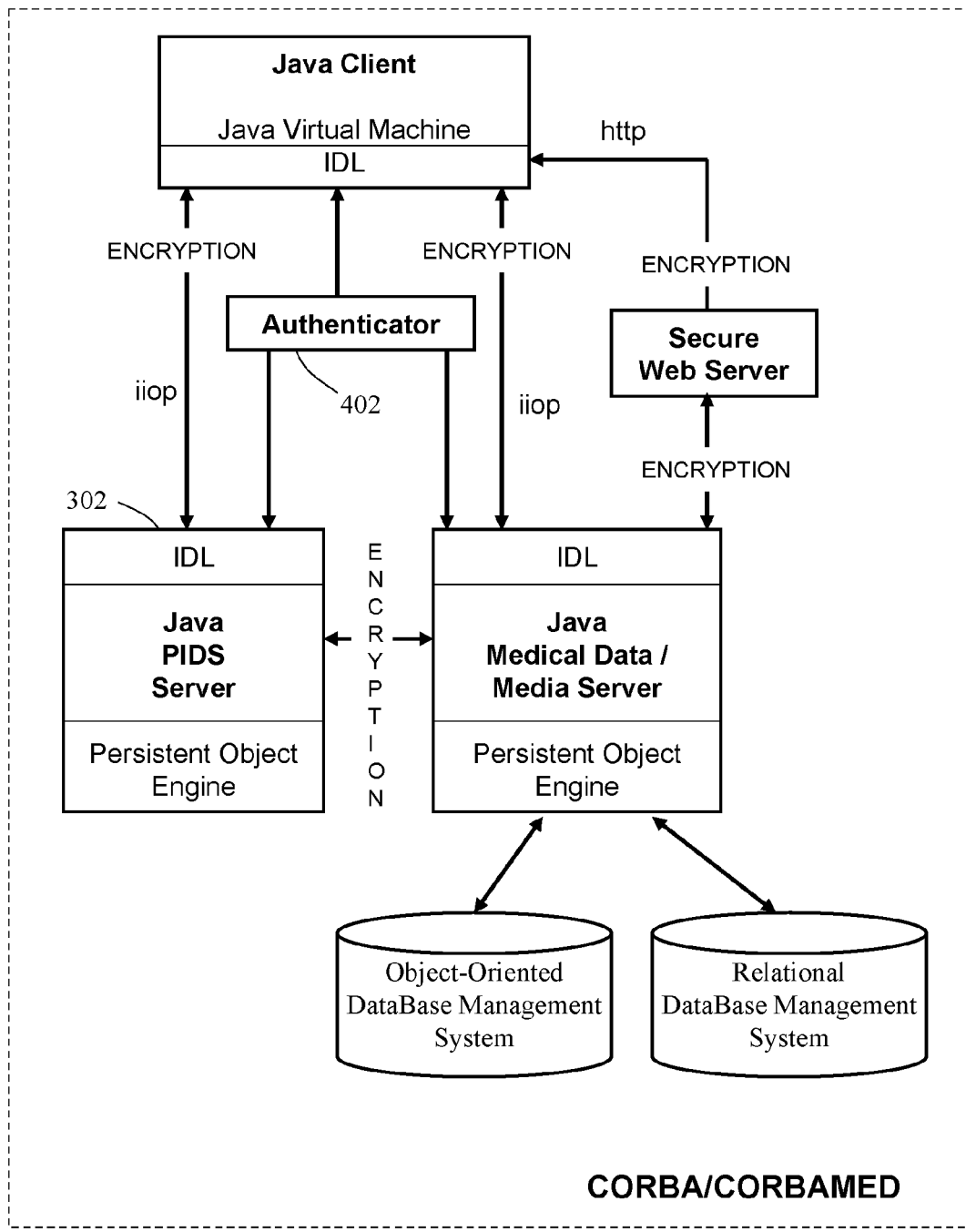
FIG. 4 illustrates another embodiment of a computer oriented record administration system incorporating a Common Object Request Broker Architecture (CORBA) in accordance with a CORBAMED standard, implemented with a modification of OpenEMed software.

OpenEMed is a Java-based, open-source implementation of the PIDS service, developed by David Forslund and colleagues at Los Alamos National Laboratory. (http://www.acl.lanl.gov/TeleMed/) OpenEMed is compliant with the emerging CORBAMED standard. Referring to FIG. 4, the CORANET software adapts several of the Java classes used by OpenEMed to communicate via CORBA with the OpenEMed PIDS server. These adapted classes can take a set of patient traits, formulate a query that is passed to the PIDS server 302, and retrieve in return a correlated ID that the PIDS server uses to represents a patient. The correlated ID returned by the PIDS server is used to create a passkey which identifies a CORANET chat session and which must be used by clients who are attempting to join the session. The construction of a passkey and creation of a session represent a transition into the third major component of the CORANET application, data transfer and interactive chat between a CORANET mobile client (the emergency medical worker) and one or more CORANET base clients (an ER physician working potentially in consultation with other specialists). The authenticator 402 (e.g. RAD service) provides for authentication of access by a client to the CORBAMED servers. The associated clients and servers each incorporate an associated Interface Definition Language (IDL), and communicate with one another using various protocols. For example, the secure web server communicates with the Java client using an http protocol, wherein the associated data is encrypted. The Java PIDS server 302 and the Java medical data server and/or media server communicate with the Java client using an Internet InterOrb Protocol (IIOP), wherein the associated data is encrypted. The data communicated between the various servers is also encrypted.

OpenEMed implements client and server versions of PIDS, COAS and RAD services, and can store and share images in JPEG and GIF format using MIME encoding. Data storage is done using an object-oriented database through JDBC interface. Information exchange in COAS is supported through XML encryption using CORBA security and standard JAVA encryption classes. The Client implements a simple COAS compliance, and the server implements the loader. A LQS (lexical component for COAS) facilitates the task of creating COAS browser support. The client is able to run from a XML enabled web browser application.

OpenEMed presently provides for sharing historical observations in COAS format only with no support for online observation (tests and inputs) and transmission. The OpenEMed software is adapted to provide for the functionality described herein. The CORANET system involves customization and integration of various components, including OpenEMed, the Precise Biometrics' fingerprint recognition SDK (Software Development Kit), and the CORALink reader and associated driver that is available for a Windows operating systems.

CORANET comprises the following three principal components: the mobile software, the base software and the Internet secure server. CORANET further comprises auxiliary components that provide administrative tools that are customized for potential users (such as the Veterans Administration (VA) or the Department of Defense (DOD)) in order to interface with other software packages used in their particular operation.

Wireless Internet systems that do not provide robust multimedia capability can be improved by caching and pre-fetching data at the Internet server level in order to obtain a required level of service as necessary to support the CORANET mobile application. Using a wireless CORANET application, the emergency room (ER) doctor can contact and collaborate with other doctors by relaying information about the case using wireless Internet-enabled PDA's or multimedia-cellular phones, for example using a wireless Internet standard, such as WASP. The workability of this extension is improved with the provision of high bandwidth wireless Internet also known as G3.

The base version of CORANET enables doctors to update patient medical charts, medical history, prescriptions and tests in accordance with standard medical emergency procedures and requirements. The CORANET-B software is adapted to provide a user-friendly and efficient interface with databases (such as standard tests and prescriptions) and fields with which doctors are accustomed to working. The base version of CORANET further provides the ability to reduce some of the administrative tasks associated with admitting a patient because all the required information is already present on the CORALink Card. The CORANET-B software is adapted to interface with other administrative software currently in use in hospitals. Hospital administrative procedures are frequently linked to requirements and procedures of insurance and healthcare organizations. CORANET-B provides for information retrieval, transmission and authorization with these organizations. The CORANET secure chat server is adapted to accommodate mobile and base capabilities identified herein.

A graphical user interface (GUI) is provided to improve efficiency in using CORANET-M and CORANET-B, since time is a critical factor in the practice of emergency medicine. The GUI is adapted in accordance with the needs of doctors and practitioners, particularly doctors and practitioners who work in emergency rooms.

CORANET further comprises system administrative software and tools associated with the operation of the CORANET system. For example, administrative tools are provided for CORALink card initialization, and for log retrieval.

CORANET further comprises a secure chat server, comprising the following elements:

1. a naming server and a trading server for Internet Contact (ORB's), for example adapted from available servers from OpenEMed;
2. a PID server, comprising the patient validation and identification part of the Internet server;
3. a RAD server comprising the authorization server that operates in accordance with a secure channel for data exchange on the secure server;
4. a COAS browser server with caching and pre-fetching capabilities for the data content of the card that accommodate a relatively poor wireless connection to the Internet on the mobile CORANET;
5. a revalidation card session for base software that allow "quick-login" by ER personnel once the patient arrives at the hospital, assuming a previous session has been started while the patient is in transit and patient validation has already been processed; and
6. a process log enabling retrieval of conversation and orders exchanged between mobile and base units.

The CORANET-M component comprises the following elements:

1. interfaces between CORANET mobile and emergency vehicle equipment, including dedicated hardware adapters and/or software drivers, as necessary;
2. an indexed double encrypted file structure that supports CORANET secure access to the card information, wherein the double encryption is based on one level to reach personal information and a secondary encryption to access medical data that is dependent on ID validation;
3. software interfaces for the fingerprint and user/password authorized access to medical data on the card;
4. a PID client—for example, adapted from OpenEMed to incorporate CORANET functionality—which, after patient identification, is used to retrieve full personal records from the PID server at the CORANET server site, wherein the cross-linked ID information allows the correct identification of the patient and patient's personal data even if the card is not updated;
5. a RAD client, which, after patient identification, is used to establish a secure channel with authorization protocol;
6. a COAS Supplier Server, which uploads the card's information as requested by the base unit, and which, for example, may be derived from the existent COAS server on OpenEMed with adaptation to support features such as index of contents, online observation and storage of data;
7. a CIAS Server for mobile COAS Support, so as to provide support for image-transfer and full compliance with CIAS server of CORBAMED to assure easy information exchange with future medical-image equipment;

8. a command line with voice exchange capability so as to provide for voice and data logging capabilities in a mobile environment; and
9. a CORANET-M GUI.

The CORANET-B component comprises the following elements:
1. a RAD client that supports login from base software to the secure channel and provides the proper authorization access;
2. a COAS Consumer Client that supports online data, remote storage on the card and browsing/caching capabilities;
3. a CORANET-B GUI;
4. command Line and voice exchange capabilities for sending/receiving written (command line) and voice commands to/from the mobile units;
5. support for Remote Syndrome Validation Project, a government-sponsored project to coordinate the reporting of any information regarding infectious diseases and the use of controlled substances to the appropriate government authorities; and
6. fast track login on card that allows "quick-login", assuming a previous session has been started while the patient is in transit and patient validation has already been processed.

CORANET V.0.01 is a Java software package that demonstrates how CORANET data-card technology can be integrated with a CORBA-based Personal Identification Service (PIDS) server in order to create a distributed system for validating and providing medical professionals with access to a patient's medical information. Using this system, emergency medical workers can access a patient's medical information in an emergency, verify a patient's identity by CORBA-based communication with a PIDS server, and communicate that information to a physician over the Internet. Using the CORANET application, the physician has access to the same medical information that the emergency medical workers do, and can provide consultation in a medical emergency using the Java-based chat client. The physician also has the potential to access a patient's medical data stored in scattered databases that are tied together using the PIDS service.

The CORANET application consists of Java-based clients that present a Graphical User Interface (GUI) with seven tabs that display different categories of the patient's medical data: personal information, family history, past medical history, physical examination results, laboratory test results, insurance information, and emergency contacts. The GUI also contains a chat area that will display the transcript of the communications that take place between emergency medical workers and an ER physician, as well as a text field for entering messages that will be transmitted to other clients. When the emergency medical workers access the patient's data card, the information stored on the card is used to populate the patient-information fields on the GUI.

Using an ordinary laptop computer equipped with a PCMCIA card slot, emergency medical workers insert the CORANET data card into the PCMCIA adaptor and insert this adapter into the slot. A Java-based login screen allows them to enter the patient's password or alternatively gain access by placing the patient's finger on the fingerprint reader. Once authentication has been accomplished, access to the patient's data is available to the Java-based CORANET mobile client, which will communicate with a PIDS server in order to authenticate the patient.

A set of traits based on data from the card is passed to the PIDS server. A PIDS query that succeeds in identifying the patient returns a unique passkey to the mobile client and initiates a session on the server that is identified using the passkey. A session resides in the server's memory, and contains information about the clients who are currently logged in to the session, representations of the patient's medical information, and an ongoing record of the current chat. The emergency medical workers must separately transfer the passkey to the physician by phone or other means. Once in possession of the passkey the physician can start up a CORANET base client and join the session.

The CORANET base client presents the same interface to the user as the mobile client, with the same set of tabs for displaying patient data and the same chat and message entry areas. The base client can be accessed as a stand alone application installed on the user's computer, and as a Web-based Java applet that the user accesses by logging onto a Web site. Login to the base client requires the passkey transmitted to the physician by the emergency medical workers. The server checks to see if a session corresponding to the passkey exists, and if so adds the base client to the session. Successful login by a CORANET client involves the initiation of sockets for network communication between the server and the client. Each client who logs on to an active session is assigned a separate port that is dedicated to communications with that particular client. The server keeps track of which ports have been assigned to which clients and uses this information to broadcast chat messages to all clients who are logged in to the session.

Once the base client has successfully joined the session, the patient's medical information that originated from the CORANET data card read by the emergency medical workers is transferred over the network to the physician's computer. The CORANET base GUI displays the same information that the emergency medical workers are seeing. When the physician joins the session using the CORANET base client, a message announcing that fact is sent to the emergency medical workers' computer. Everything is now ready for the medical technicians to communicate with the physician using chat messages over the network. When any currently logged in to the active session types in a message and hits "Enter", that message is immediately broadcast to all clients that are also participating in the session and appears in the chat area of each client.

In this way, the physician is able to consult with the medical technicians as they provide care to the patient and can do so in full knowledge of the patient's medical history as retrieved from the CORANET card. In one embodiment both emergency medical workers and physician may edit the data on the card. In another embodiment, different users have different levels of access authority. The medical technicians do so directly, since the CORANET application writes the data entered in the GUI to the files stored on the data card. The physician may also write to the card, but does so remotely, passing the new information he enters over the network via the server to the medical technicians' computer, where it is finally written onto the CORANET data card. Any updates to the data on the card are also transmitted over the network to the other clients and are displayed in the fields of the client's GUIs. Each client is therefore presented with the current state of the data contained on the patient's data card. Not all of the fields may be edited, however. Text entry is disabled on those fields that cannot be edited by medical technicians or the physician.

The CORANET mobile client continues the chat session with one or more CORANET base clients as long as necessary. The session exists as long as a single client is still logged in to the session. A physician may join the session on one computer, for example, and after consulting with the technicians may log out of the session. The session still exists as long as the CORANET mobile client is still logged on to the system. The physician can move to a different computer (for example, one located in the hospital to which the patient is being transported), rejoin the session, and continue to chat with the technicians. Additional specialists from other locations may join the session as needed, provide consultation, and then log out. The server keeps track of all the clients who are currently participating in the session and records the time they join and leave the session, as well as the transcript of their chat messages.

Once all of the clients have logged out of the session, a log of the session is written to the server's file system. The log clearly shows when each client joins and leaves the session, and displays the exact transcript of the chat messages that were exchanged, identifying who sent the message and displaying a time stamp of when the message was sent. The transcript provides an accurate historical record of the actual communication that took place between the emergency medical workers and the physician and other specialists with whom they were in consultation. Besides being written to a file, the session log could easily be stored in a database using the passkey as an identifier.

After all the clients have left the session and the log has been written, the session is officially closed and is removed from the server's memory. No more communication can take place in this session, but a new session may be initiated for the same patient by the emergency medical technicians or by the ER physician, who could become the "mobile" user once the patient has arrived at the hospital thereby giving the physician direct access to the CORANET data card. The physician could in turn transmit the passkey to other specialists who could provide consultation to the ER physician using the same chat mechanism as the physician used with the emergency medical technicians but in a newly initiated session.

The operation of CORANET is now further illustrated in the context of examples of various scenarios for various 1) entities that might be involved in an emergency, and 2) computer hardware and software, and Internet access capabilities that might be available to each of these entities, wherein the following assumptions apply to all scenarios:

1. The personnel involved have a basic familiarity with computers and the Internet;
2. All personnel/facilities have a computer with associated hardware capable of loading the CORALink data card that contains medical records; and
3. Not all personnel/facilities have access to required hardware and software to read a patient's fingerprint. When fingerprint reading is not possible it is assumed that the patient is conscious and can provide the emergency personnel with the password to access his/her medical data.

The terminology used to denote the different personnel and equipment that might be involved in a medical emergency rescue operation is defined as follows:

Patient: Person in need of medical assistance, having a CORALink data/fingerprint card.

Skilled Practitioner: Medical personnel attending the patient. It is assumed here that the practitioner is trained to use the CORALinks card and associated software. The practitioner is registered at the CORANET website and can download "mobile" software that allows reading and writing to the data card, with no read or write access to private nodes.

Unskilled Practitioner: Person attending the patient, not "medically qualified". The practitioner is not registered at the CORANET website and can download "mobile" software that allows reading of data card (no write permission to the data card) with no read or write access to private nodes.

Doctor: Medical Doctor. The doctor is registered at the CORANET website and can download "mobile/base" software that allows reading and writing to the data card with read and write access to private notes.

Equipped Computer: Computer with proper CORALink software and/or hardware installed.

Unequipped Computer: Computer without proper CORALink software and/or hardware installed.

Private notes: Specially marked information stored on the card that is accessible only by a doctor.

A first scenario comprises a medical emergency wherein a skilled medical practitioner (paramedic, nurse etc) in an ambulance is attending to the patient and can contact an ER doctor, in accordance with the following assumptions: 1) the ambulance has required software/hardware to unlock the card along with password or fingerprint access; 2) the ambulance has wireless Internet access; 3) the ER has required software/hardware to unlock the card along with password or fingerprint access; 4) a voice log is recorded at the hospital and/or a central location; 5) the doctor at emergency room has full access to private notes but the practitioner at the ambulance does not have access to private notes; and 6) the patient can be conscious or unconscious. In accordance with this first scenario, the skilled practitioner first unlocks the card using the password or fingerprint access card and reader, then starts the "mobile software" which registers with a secure "chat" server on the Internet, and then contacts the emergency room and relays the chat room pass key to the ER doctor. Using the key, the ER doctor from emergency room starts the "base software" on the ER computers, establishes a contact through the chat server, and accesses the patient's medical records which includes the private notes. Then using either text-messages or voice-over-net technology, the doctor instructs the paramedics regarding the appropriate course of action, and simultaneously updates the medical files. Upon arrival of the patient at the emergency room, the doctors plugs the data card into the ER computers, directly accesses/updates the patient's medical records, and performs necessary medical procedures.

A second scenario comprises a medical emergency wherein a skilled/unskilled medical practitioner is attending to the patient and can contact a doctor, in accordance with the following assumptions: 1) the practitioner's computer does not have required software/hardware to unlock the card along with password or fingerprint access, 2) the patient is conscious; and 3) the doctor and practitioner need not have a computer with "mobile/base" CORANET software. In accordance with this second scenario, the doctor/skilled/unskilled practitioner plugs the card into the appropriate adapter and then access the CORANET web-page via the Internet and identifies himself/herself as the doctor/skilled practitioner. The skilled practitioner/doctor uses a password for identification, which allows for the maintenance of a log on the server. Depending on whether the user is a doctor or skilled practitioner, the proper Java applet is downloaded. The skilled practitioner unlocks the card using the password or fingerprint access card and reader, and starts "mobile software" which registers with a secure "chat" server on Internet. The practitioner contacts the doctor and relays the chat room passkey to the doctor. Using the key, the doctor establishes a contact through the "chat" server and accesses the patient's medical records, which include private notes. Using either text-messages or voice-over-net technology the doctor instructs the paramedics regarding the appropriate course of action, and simultaneously updates the medical files.

A third scenario comprises a medical emergency wherein a doctor/skilled/unskilled medical practitioner is attending to the patient, but without involvement of an ER doctor, in accordance with the following assumptions: 1) The doctor/skilled/unskilled practitioner has required hardware (for example if the only hardware required was a PCMCIA slot) to load the card but does not have associated CORANET "mobile software" to unlock the card and access medical data thereon; and 2) the computer has Internet access. In accordance with this third scenario, the doctor/skilled/unskilled practitioner plugs the card into the appropriate adapter and accesses the CORALinks emergency page via the Internet and identifies himself/herself as a skilled/unskilled practitioner. The skilled practitioner uses his/her password to identify himself, which enables the maintenance of a log on the server. Depending on whether the practitioner is a doctor, skilled or unskilled, the proper Java applet is downloaded. The doctor and skilled practitioner can update the card.

A fourth scenario comprises an office consultation with a doctor, wherein the doctor's office is assumed to have the software/hardware required to unlock the card. In accordance with this fourth scenario, the patient visits the doctor's office, and the doctor plugs the card in the computer and uses the proper software to unlock it using the patient's password. The doctor then gains read and write access to the card and can import and export files therewith, and can interface with his or her preferred medical record software.

The portable memory element 22 (or CORALink card) can be adapted to securely store a variety of data, in accordance with a variety of formats that are compatible with a various health information systems. For example, FIG. 5 tabulates the information that could be stored for the following associated health information systems: I) VISTA SYSTEM—Veterans Health Information Systems and Technology Architecture (Veterans Affairs); II) CHCS—Composite Health Care System (Department of Defense); IIIA) private sector inpatient/outpatient services; and IIIB) private sector emergency services.

While specific embodiments have been described in detail in the foregoing detailed description and illustrated in the accompanying drawings, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

I claim:

1. A method of providing for a server on a computer, comprising:
   a. providing for communicating with a first client, wherein said first client performs a method comprising:
      i. providing for reading a portable memory element;
      ii. providing for obtaining passcode information necessary to access data from said portable memory element; and
      iii. providing for authenticating said passcode information;
   b. providing for providing a passkey to said first client if said passcode information is authentic for said portable memory element;
   providing for communicating with at least one second client;
   d. providing for receiving a passkey from said at least one second client; and
   e. providing for enabling said at least one second client to communicate with said first client if a value of said passkey received from said at least one second client corresponds to a value of said passkey provided to said first client.

2. A method of providing for a server on a computer as recited in claim 1, wherein the operation of providing for communicating with said first client comprises providing for encrypting signals that are sent to said first client, and decrypting signals that are received from said first client.

3. A method of providing for a server on a computer as recited in claim 1, wherein said portable memory element comprises a memory card, a flash memory card or a SmartCard.

4. A method of providing for a server on a computer as recited in claim 1, wherein said data comprises medical information of a person who is capable of providing said passcode information necessary to access data from said portable memory element.

5. A method of providing for a server on a computer as recited in claim 1, wherein said passcode information comprises at least one fingerprint of a person associated with said portable memory element.

6. A method of providing for a server on a computer as recited in claim 1, wherein said passcode information comprises either alphanumeric information or biometric information provided by a person associated with said portable memory element.

7. A method of providing for a server on a computer as recited in claim 1, wherein said first client is mobile.

8. A method of providing for a server on a computer as recited in claim 1, further comprising providing for enabling said first client either to read information from, or to record information to, said portable memory element if said passcode information is authentic for said portable memory element.

9. A method of providing for a server on a computer as recited in claim 8, wherein said information recorded to said portable memory element comprises voice information, data from a medical instrument, data from a keyboard or keypad, or handwritten data.

10. A method of providing for a server on a computer as recited in claim 1, further comprising identifying a level of authority of said first client, and controlling access to said data responsive to said level of authority.

11. A method of providing for a server on a computer as recited in claim 1, further comprising providing for a first user associated with said first client to provide said passkey to said at least one second user associated with at least one second client so that said at least one second user can provide said passkey having said value that corresponds to said value of said passkey provided by said first client.

12. A method of providing for a server on a computer as recited in claim 1, wherein the operation of providing for communicating with said at least one second client comprises providing for encrypting signals that are sent to said at least one second client, and decrypting signals that are received from said at least one second client.

13. A method of providing for a server on a computer as recited in claim 1, further comprising providing for enabling said at least one second client either to read information from, or to record information to, said portable memory element if said value of said passkey provided by said at least one second client corresponds to said value of said passkey provided to said first client.

14. A method of providing for a server on a computer as recited in claim 1, further comprising providing for interfacing with a CORBAMED system.

15. A method of providing for a server on a computer as recited in claim 14, wherein said CORBAMED system comprises a Terminology Query Service server, a Clinical Observation Access Service server, and a Resource Access Decision server.

16. A method of providing for a server on a computer as recited in claim 15, further comprising providing for said first client to read at least one trait from said portable memory element and providing for receiving said at least one trait from said first client.

17. A method of providing for a server on a computer as recited in claim 16, further comprising communicating said at least one trait to said CORBAMED system and communicating data from said CORBAMED system corresponding to said at least one trait to at least one of said first client and said at least one second client.

18. A method of providing for a server on a computer as recited in claim 16, wherein said at least one trait is defined in accordance with a Health Level 7 (HL7) specification.

19. A method of providing for a server on a computer as recited in claim 16, further comprising storing information from either said first client or said at least one second client in at least one database operatively associated with said CORBAMED system.

20. A Personal Identification Service server of a CORBAMED system, comprising:
   a. a means for communicating with a first client;
   b. a means for receiving a first signal from said first client, wherein said first signal indicates if said first client is authorized to access a portable memory element provided that said portable memory element is operatively connected to said first client;
   c. a means for providing a passkey to said first client if said first signal indicates that said first client is authorized to access said portable memory element;
   d. a means for communicating with at least one second client;
   e. a means for receiving a second signal from said at least one second client; and
   f. a means for providing for said at least one second client to communicate with said first client if said second signal comprises a passkey having a value that corresponds to a value of said passkey provided to said first client.

21. A Personal Identification Service server of a CORBAMED system as recited in claim 20, further comprising a means for providing for said first client to either read information from, or record information to, said portable memory element if said first signal indicates that said first client is authorized to access said portable memory element.

22. A Personal Identification Service server of a CORBAMED system as recited in claim 20, further comprising a means for providing for said at least one second client to either read information from, or record information to, said portable memory element if said second signal comprises said passkey having said value that corresponds to said value of said passkey provided to said first client.

23. A method of providing for a first client on a computer, comprising:

a. providing for communicating with a server;
   b. providing for reading a portable memory element;
   c. providing for obtaining passcode information necessary to access data from said portable memory element;
   d. providing for authenticating said passcode information;
   e. providing for receiving a first passkey from said server if said passcode information is authentic for said portable memory element; and
   f. providing for communicating with at least one second client in communication with said server.

24. A method of providing for a first client on a computer as recited in claim 23, further comprising providing for a first user associated with the first client to provide said first passkey to at least one second user associated with said at least one second client.

25. A method of providing for a first client on a computer as recited in claim 23, wherein the operation of providing for communicating with said server comprises providing for encrypting signals that are sent to said server, and decrypting signals that are received from said server.

26. A method of providing for a first client on a computer as recited in claim 23, wherein said portable memory element comprises a memory card, a flash memory card or a SmartCard.

27. A method of providing for a first client on a computer as recited in claim 23, wherein said data comprises medical information of a person who is capable of providing said passcode information necessary to access data from said portable memory element.

28. A method of providing for a first client on a computer as recited in claim 23, wherein said passcode information comprises at least one fingerprint of a person associated with said portable memory element.

29. A method of providing for a first client on a computer as recited in claim 23, wherein said passcode information comprises either alphanumeric information or biometric information provided by a person associated with said portable memory element.

30. A method of providing for a first client on a computer as recited in claim 23, further comprising providing for either reading information from, or recording information to, said portable memory element if said passcode information is authentic for said portable memory element.

31. A method of providing for a first client on a computer as recited in claim 30, wherein said information from said first client comprises voice information, data from a medical instrument, data from a keyboard or keypad, or handwritten data.

32. A method of providing for a first client on a computer as recited in claim 23, further comprising identifying a level of authority, and controlling access to said data responsive to said level of authority.

33. A first client computer system, comprising:
   a. a computer;
   b. a memory interface device operatively connected to said computer, wherein said memory interface device is capable of interfacing with a portable memory element;
   c. a data input device operatively connected to said computer, wherein said data input device provides for entering passcode information necessary to access data on said portable memory element when said portable memory element is operatively connected to said memory interface device;
   d. a communications interface operatively connected to said computer and to at least one other computer;

e. a memory, wherein said memory provides for storing an application program, wherein said application program provides for a method comprising:
  i. providing for communicating via said communications interface with a server;
  ii. providing for reading said portable memory element provided that said portable memory element is operatively connected to said memory interface device;
  iii. providing for obtaining said passcode information from said data input device necessary to access said data from said portable memory element;
  iv. providing for authenticating said passcode information;
  v. providing for receiving a first passkey from said server if said passcode information is authentic for said portable memory element;
  vi. providing for a first user associated with the first client computer system to provide said first passkey to at least one second user associated with at least one second client computer system; and
  vii. providing for communicating information via said communications interface with said at least one second client computer system in communication with said server.

34. A first client computer system as recited in claim 33, wherein said data input device comprises a fingerprint reader operatively connected to said computer, and the operation of obtaining said passcode information from said data input device comprises reading at least one fingerprint with said fingerprint reader.

35. A first client computer system as recited in claim 33, wherein said communications interface is operatively connected to a computer network.

36. A first client computer system as recited in claim 35, wherein said communications interface comprises a wireless communication device.

37. A first client computer system as recited in claim 33, wherein said communications interface comprises a wireless communication device.

38. A first client computer system as recited in claim 33, further comprising providing for storing said information on said portable memory element.

39. A first client computer system as recited in claim 33, further comprising providing for reading stored information from said portable memory element and either displaying said stored information with a display operatively connected to said computer or communicating said stored information to said at least one second client computer system.

40. A portable memory element, comprising a memory capable of being read from or written to by a computer provided that said memory is operatively connected to a first client computer system, wherein said memory is adapted to store passcode information as stored passcode information, and said memory provides for cooperating with said first client computer system that operates in accordance with a method comprising:
  a. providing for communicating by said computer via a communication interface with a server;
  b. providing for reading said portable memory element by said first client computer system provided that said memory is operatively connected to a memory interface device of said first client computer system;
  c. providing for obtaining passcode information from a data input device operatively connected to said first client computer system, wherein said passcode information is necessary to access data from said memory;
  d. providing for authenticating said passcode information by comparing said passcode information with said stored passcode information;
  e. providing for receiving a first passkey from said server if said passcode information matches said stored passcode information;
  f. providing for a first user associated with said first client computer system to provide said first passkey to at least one second user associated with at least one second client computer system; and
  g. providing for communicating information via said communication interface with said at least one second client computer system in communication with said server.

41. A portable memory element as recited in claim 40, wherein the operation of obtaining said passcode information from said data input device comprises reading at least one fingerprint with a fingerprint reader operatively connected to said first client computer system.

42. A portable memory element as recited in claim 40, further comprising providing for storing said information in said memory.

43. A portable memory element as recited in claim 40, further comprising providing for reading stored information from said memory and either displaying said stored information with a display operatively connected to said first client computer system or communicating said stored information to said at least one second client computer system.

* * * * *